(12) United States Patent
Hayashi et al.

(10) Patent No.: US 9,816,944 B2
(45) Date of Patent: Nov. 14, 2017

(54) METHOD FOR EVALUATING OXIDE SEMICONDUCTOR THIN FILM, METHOD FOR MANAGING QUALITY OF OXIDE SEMICONDUCTOR THIN FILM, AND EVALUATION ELEMENT AND EVALUATION DEVICE USED IN ABOVE EVALUATION METHOD

(71) Applicant: Kobe Steel, Ltd., Hyogo (JP)

(72) Inventors: Kazushi Hayashi, Kobe (JP); Aya Miki, Kobe (JP); Toshihiro Kugimiya, Kobe (JP); Nobuyuki Kawakami, Kobe (JP)

(73) Assignee: Kobe Steel, Ltd., Hyogo (JP)

( * ) Notice: Subject to any disclaimer, the term of this patent is extended or adjusted under 35 U.S.C. 154(b) by 87 days.

(21) Appl. No.: 15/031,990

(22) PCT Filed: Dec. 1, 2014

(86) PCT No.: PCT/JP2014/081744
§ 371 (c)(1),
(2) Date: Apr. 25, 2016

(87) PCT Pub. No.: WO2015/083666
PCT Pub. Date: Jun. 11, 2015

(65) Prior Publication Data
US 2016/0282284 A1  Sep. 29, 2016

(30) Foreign Application Priority Data

Dec. 3, 2013 (JP) .................................. 2013-250412
May 20, 2014 (JP) .................................. 2014-104629

(51) Int. Cl.
*H01L 29/786* (2006.01)
*G01N 22/00* (2006.01)
(Continued)

(52) U.S. Cl.
CPC ............. *G01N 22/00* (2013.01); *G01N 21/63* (2013.01); *G01N 21/8422* (2013.01);
(Continued)

(58) Field of Classification Search
CPC ............. H01L 29/7869; H01L 27/1225; H01L 29/66969; H01L 21/02565;
(Continued)

(56) References Cited

U.S. PATENT DOCUMENTS

2009/0252891 A1* 10/2009 Hirata .................. H01L 27/28
427/553
2012/0203473 A1   8/2012 Hayashi et al.
(Continued)

FOREIGN PATENT DOCUMENTS

CN       102313849 A      1/2012
JP       2002-098634 A    4/2002
(Continued)

OTHER PUBLICATIONS

International Search Report issued in PCT/JP2014/081744; dated Mar. 3, 2015.
(Continued)

*Primary Examiner* — Alesa Allgood
(74) *Attorney, Agent, or Firm* — Studebaker & Brackett PC

(57) ABSTRACT

The present invention provides a method for accurately and easily measuring/evaluating/predicting/estimating the electrical resistance of an oxide semiconductor thin film, and a method for managing the film quality. The method for evaluating an oxide semiconductor thin film includes: a first step for irradiating, with excitation light and microwave, a sample on which an oxide semiconductor thin film is formed, measuring the maximum value of the reflected microwave by the thin film which changes due to the
(Continued)

excitation light irradiation, then stopping the excitation light irradiation and measuring the change in reflectivity of the microwave from the thin film after the excitation light irradiation has been stopped; and a second step for calculating a parameter corresponding to the slow decay observed after the excitation light irradiation has been stopped from the change in the reflectivity and evaluating the electrical resistivity of the oxide semiconductor thin film.

20 Claims, 7 Drawing Sheets

(51) Int. Cl.
H01L 21/66 (2006.01)
G01N 21/84 (2006.01)
G01N 21/63 (2006.01)
G01N 27/04 (2006.01)

(52) U.S. Cl.
CPC .............. *G01N 27/04* (2013.01); *H01L 22/12* (2013.01); *H01L 29/7869* (2013.01); *H01L 22/14* (2013.01)

(58) Field of Classification Search
CPC ................ H01L 21/02631; H01L 29/24; H01L 29/78696; H01L 29/78606; H01L 51/5234
See application file for complete search history.

(56) References Cited

U.S. PATENT DOCUMENTS

| 2013/0153778 A1 | 6/2013 | Sakoda et al. |
| 2015/0355095 A1 | 12/2015 | Hayashi et al. |
| 2015/0371906 A1 | 12/2015 | Kishi et al. |

FOREIGN PATENT DOCUMENTS

| JP | 2010-123872 A | | 6/2010 | |
| JP | 2011-054863 A | | 3/2011 | |
| JP | 2012-033857 A | | 2/2012 | |
| JP | 2012033857 | * | 2/2012 | .............. G01N 22/00 |
| TW | 201226892 A | | 7/2012 | |

OTHER PUBLICATIONS

Written Opinion issued in PCT/JP2014/081744; dated Mar. 3, 2015.
Kenji Nomura et al.; "Amorphous Oxide Semiconductors for High-Performance Flexible Thin-Film Transistors"; Japanese Journal of Applied Physics; 2006; pp. 4303-4308; vol. 45, No. 5B; The Japan Society of Applied Physics.
Kenji Nomura et al.; "Room-temperature fabrication of transparent flexible thin-film transistors using amorphous oxide semiconductors"; Nature; Nov. 25, 2004; pp. 488-492; vol. 432; Nature Publishing Group.

* cited by examiner 41 42 43

41 42 43

41 42 43 44

41  42  43  44  48

41       43

41   42   43   44

41     43    44

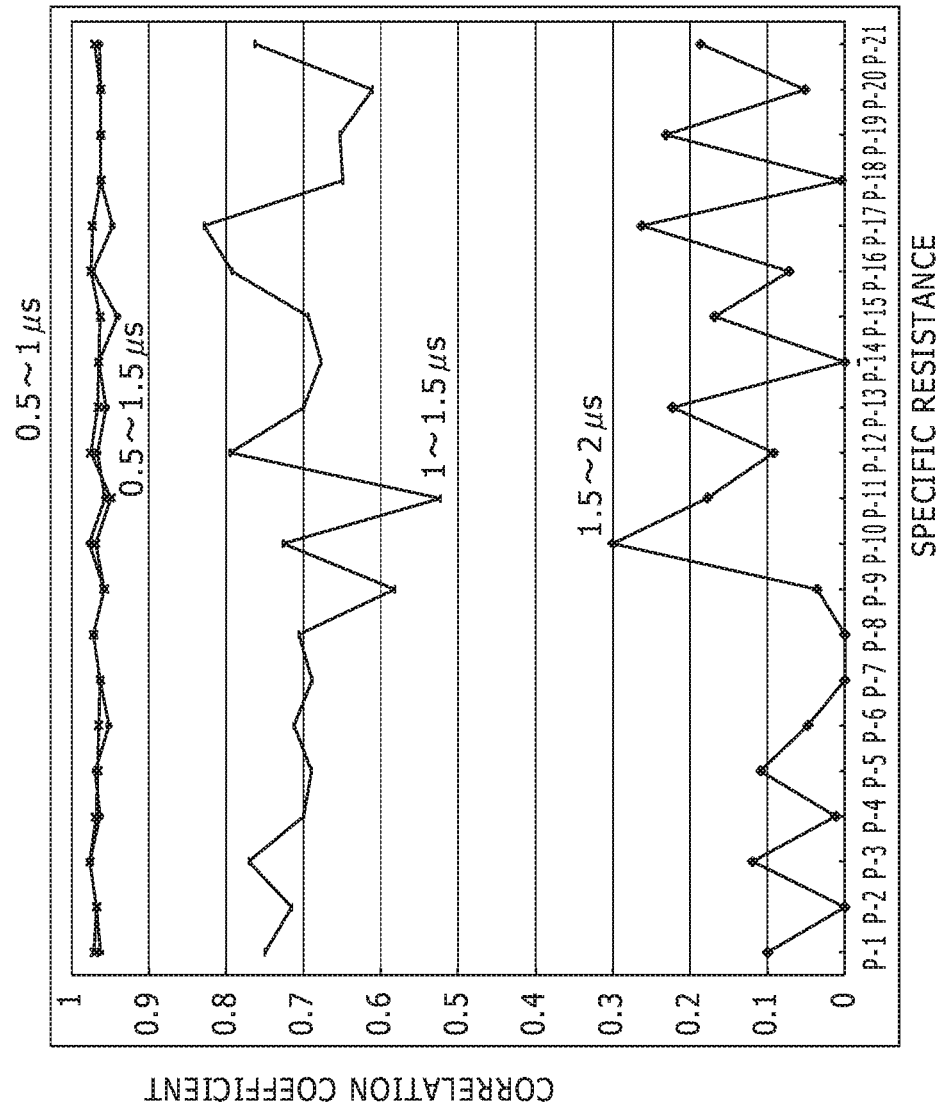

METHOD FOR EVALUATING OXIDE SEMICONDUCTOR THIN FILM, METHOD FOR MANAGING QUALITY OF OXIDE SEMICONDUCTOR THIN FILM, AND EVALUATION ELEMENT AND EVALUATION DEVICE USED IN ABOVE EVALUATION METHOD

TECHNICAL FIELD

The present invention relates to an evaluation method and a quality control method of an oxide for a semiconductor layer, i.e., an oxide semiconductor thin film, of a thin film transistor used in displays such as a liquid crystal display or an organic EL display, and an evaluation element and an evaluation device used in the evaluation method. In detail, the invention relates to a technology for nondestructively determining and evaluating sheet resistance or specific resistance (hereinafter, also referred to as "electrical resistivity") of the oxide semiconductor thin film.

BACKGROUND ART

Amorphous oxide semiconductor thin films have high carrier mobilities, wide bandgaps, and can be formed at low temperatures compared with amorphous silicon, and are to be applied to a next-generation display to which large size, high resolution, and high-speed drive are required.

Among the oxide semiconductor thin films, an amorphous oxide semiconductor thin film including indium (In), gallium (Ga), zinc (Zn), and oxygen (O) (hereinafter, also referred to as In—Ga—Zn—O or IGZO) has been preferably used because of its extremely high carrier mobility. For example, in the disclosures of NPTLs 1 and 2, an oxide semiconductor thin film including In, Ga, and Zn (In Ga:Zn=1.1:1.1:0.9 in atomic percent) is used as an active semiconductor layer of TFT. PTL 1 further discloses an amorphous oxide containing Mo and an element such as In, Zn, Sn, or Ga, in which an atomic composition ratio of Mo to the total number of metal atoms in the amorphous oxide is 0.1 to 5 atomic percent. PTL 1 discloses a TFT having an active layer comprising IGZO and Mo.

Properties of the oxide semiconductors are, however, known to vary depending on various deviations in the course of film formation process and subsequent heat treatment. For example, TFT characteristics are liable to deviate by significant change of carrier concentrations, a dominant factor of TFT characteristics, caused by lattice defects and hydrogen in the film generated in the course of the film formation process. It is thus essential from the point of view to improving the productivity to evaluate properties of deposited oxide semiconductor thin films, to feedback the results of the evaluation, to adjust manufacturing conditions, and to control film quality in the manufacturing process of the display devices or the like.

In typical characterization methods, mobility and carrier density of oxide semiconductor thin films are evaluated by Hall-effect measurement after forming a gate insulating film or a passivation insulating film on an oxide semiconductor thin film, and an electrode having a predetermined size on the insulating film via lithography using a metal mask.

It takes, however, time and cost to form contact electrodes in such a contacting type evaluation method. Formation of the contact electrodes is also liable to induce additional defects in the oxide semiconductor thin film. It is thus required to establish a contactless-type evaluation method in which formation of contact electrodes is not necessary from the point of view to improving fabrication yield.

The existing evaluation methods involving the electrode provision suffer from difficulties such as low spatial resolution and long measurement time.

PTL 2 discloses a method for controlling film quality in a noncontact manner without forming an electrode, in which mobility of an oxide semiconductor thin film is qualitatively or quantitatively evaluated by a microwave photoconductive decay method.

CITATION LIST

Patent Literature

PTL 1: Japanese Unexamined Patent Application Publication No. 2009-164393
PTL 2: Japanese Unexamined Patent Application Publication No. 2012-33857

Nonpatent Literature

NPTL 1: KOTAI BUTSURI (SOLID STATE PHYSICS), vol. 44, p. 621, 2009
NPTL 2: Nature, vol. 432, p. 488, 2004

SUMMARY OF INVENTION

Technical Problem

The present invention has been made under the circumstances described above, and one object of the present invention is to provide a method to accurately and easily measure and evaluate (predict or estimate) electrical resistivity of an oxide semiconductor thin film, and to provide a method of quality control of the oxide semiconductor thin film.

Another object of the invention is to provide an evaluation element and an evaluation device used in the evaluation method.

Solution to Problem

A method for evaluating an oxide semiconductor thin film according to the invention, which has succeeded in achieving the above-described goal, includes: a first step of irradiating excitation light and microwave to an oxide semiconductor thin film, measuring the maximum of a reflected microwave from the oxide semiconductor thin film, which varies with the irradiation of the excitation light, and then stopping the irradiation of the excitation light and measuring a temporal variation in the reflectance from the oxide semiconductor thin film after stopping the excitation light irradiation; and a second step of calculating a parameter corresponding to slow decay observed after stopping the irradiation of the excitation light based on the temporal variation in the reflectivity, and evaluating electrical resistivity of the oxide semiconductor thin film.

In a preferred embodiment of the invention, the electrical resistivity corresponds to sheet resistance or specific resistance.

In a preferred embodiment of the invention, in the second step, the parameter corresponding to the slow decay observed at 0.1 to 10 µs after stopping irradiation of the excitation light is calculated based on the variation in reflectivity to evaluate the electrical resistivity of the oxide semiconductor thin film.

In a preferred embodiment of the invention, the oxide semiconductor thin film contains at least one element selected from the group consisting of In, Ga, Zn, and Sn.

In a preferred embodiment of the invention, the oxide semiconductor thin film is provided on a surface of a gate insulating film.

In a preferred embodiment of the invention, the oxide semiconductor thin film has a passivation film on its surface.

A method for controlling quality of an oxide semiconductor thin film according to the invention, which has succeeded in solving the above-described problem, is a method for evaluating the oxide semiconductor thin film is applied to one of steps of a semiconductor manufacturing process.

The invention includes a quality control system of an oxide semiconductor thin film, in which the above-described quality control method is used in one of steps of a semiconductor manufacturing process.

An evaluation element of the invention, which has succeeded in solving the above-described problem, is used in one of the above-described evaluation methods, and including an oxide semiconductor thin film provided on a substrate.

In a preferred embodiment of the invention, the oxide semiconductor thin film is directly provided on the surface of the substrate.

In a preferred embodiment of the invention, the oxide semiconductor thin film is directly provided on the surface of the gate insulating film.

In a preferred embodiment of the invention, a passivation film is provided on the surface of the oxide semiconductor thin film.

An evaluation device of the invention, which has succeeded in solving the above-described problem, includes a plurality of evaluation elements arranged on a substrate, each evaluation element being one of the above-described evaluation elements.

According to a further preferred embodiment of the invention, there is provided a system used in the method for evaluating the oxide semiconductor thin film, the system including an excitation light irradiation unit that irradiates excitation light to a measurement site of an oxide semiconductor thin film to generate electron-hole pairs in the oxide semiconductor thin film, a microwave irradiation unit that irradiates a microwave to the measurement site of the sample, a reflected microwave intensity detection unit that detects intensity of a reflected microwave from the oxide semiconductor thin film due to reflection of the microwave, the intensity being varied by the excitation light irradiation, and a unit for evaluating electrical resistivity of the semiconductor thin film based on the detection data of the reflected microwave intensity detection unit.

In another preferred embodiment, the evaluation system of the oxide semiconductor thin film of the invention further includes an electrical resistance measurement unit having an electrical resistivity measurement head and an up-and-down unit for the electrical resistivity measurement head.

Advantageous Effects of Invention

According to the invention, the electrical resistivity of the oxide semiconductor thin film can be accurately and easily evaluated, predicted, and measured.

Applying the evaluation method of the invention to one of steps of a semiconductor manufacturing process allows quality control of the oxide semiconductor thin film during a manufacturing process of a TFT.

According to the invention, there are also provided an evaluation element and an evaluation device used in each of the above-described steps.

BRIEF DESCRIPTION OF DRAWINGS

FIG. 12B is a chart illustrating results of the second embodiment, showing a relationship between the specific resistance at each measurement point on the substrate and a correlation coefficient.

DESCRIPTION OF EMBODIMENTS

Figure 1:
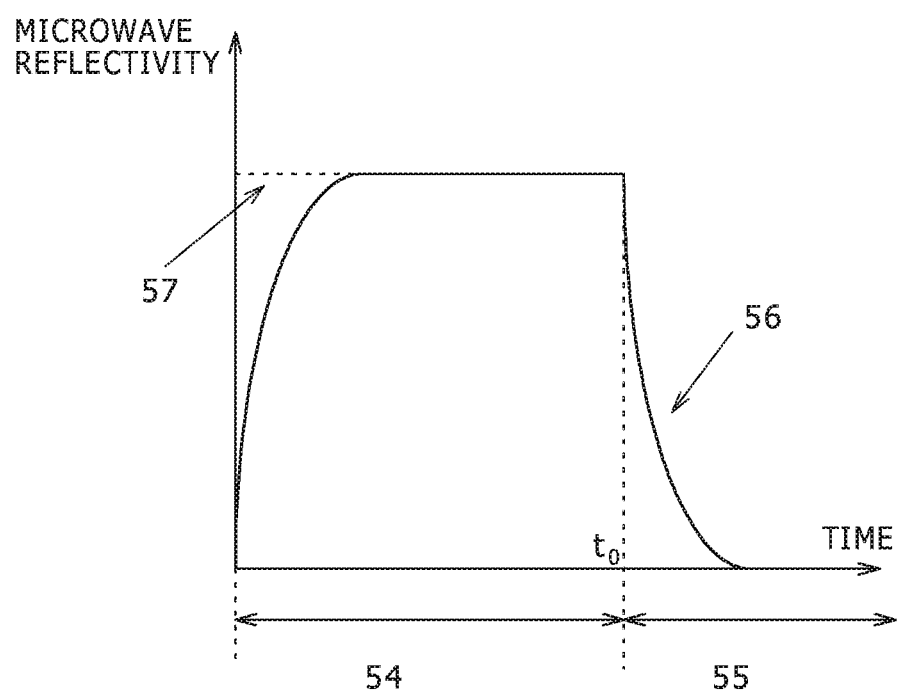
FIG. 1 is a diagram illustrating an exemplary microwave decay waveform.
Figure 2:
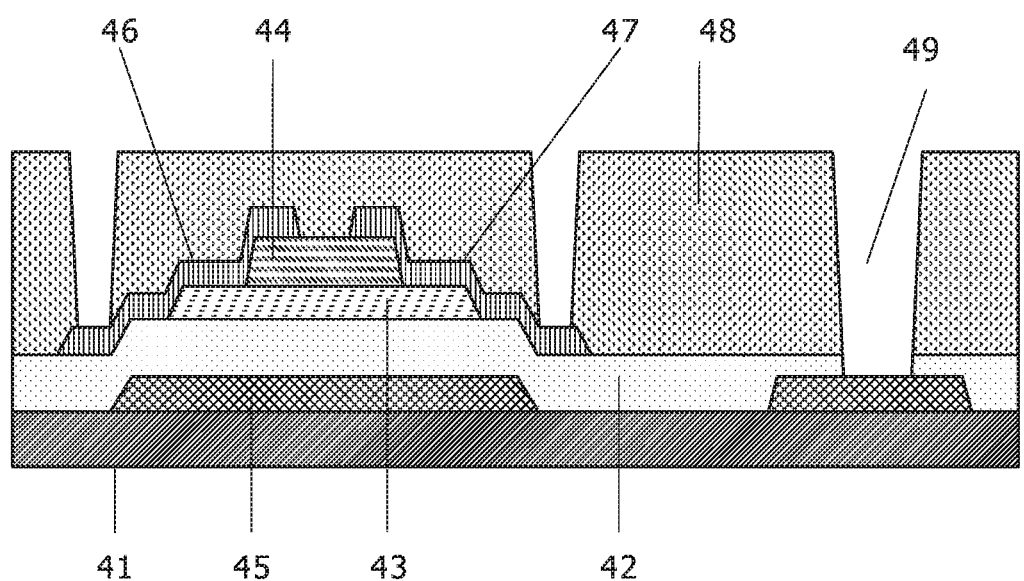
FIG. 2 is a schematic diagram illustrating a structure of oxide semiconductor TFT used in first and second embodiments.

An evaluation method of an oxide semiconductor thin film according to the invention includes: a first step of irradiating excitation light and microwave to an oxide semiconductor thin film, measuring the maximum of a reflected microwave from the oxide semiconductor thin film, which varies with the irradiation of the excitation light, and then stopping the irradiation of the excitation light and measuring a temporal variation in the reflectance from the oxide semiconductor thin film after stopping the excitation light irradiation; and a second step of calculating a parameter corresponding to slow decay observed after stopping the irradiation of the excitation light based on the temporal variation in reflectivity, and evaluating the electrical resistivity of the oxide semiconductor thin film. The electrical resistivity includes sheet resistance (Ω·cm/□) and specific resistance (Ω·cm). The specific resistance corresponds to the product of the sheet resistance and thickness.

Specifically, the invention uses the microwave photoconductive decay method described in PTL 2. In detail, the features of the invention are based on the following two findings. That is, a slow microwave decay waveform, which is part of microwave decay provided by the method of PTL 2 and observed after stopping the irradiation of the excitation light, i.e., a degree of microwave decay is greatly affected by a defect level below the conduction band of the oxide semiconductor thin film. In addition, analysis of a signal in such a region below the conduction band is therefore extremely useful as an index that allows accurate and easy evaluation, prediction, and measurement of information on electrical resistivity of the oxide semiconductor thin film and on carrier concentration.

In the phrase of "parameter corresponding to slow decay observed after stopping excitation light irradiation" in this description, "slow decay" means time in a predetermined span after stopping excitation light irradiation. Although specific time varies depending on types of the oxide semiconductor and is difficult to be uniquely determined, the time generally means 0.1 to 10 μs after stopping the excitation light irradiation. The time span is preferably 0.15 to 2.0 μs, and more preferably 0.2 to 1.0 μs after stopping the excitation light irradiation.

A state of "slow decay" generally varies depending on types of an oxide semiconductor as the sample. Hence, as described below, the meaning of "slow decay" also includes the range of microwave reflectivity after reflectivity decay becomes slow, i.e., a slope of a decay waveform becomes small after stopping the irradiation of the excitation light. The region of "slow decay" should be appropriately set in a span where the decay having a certain slope, which is observed after a region where the reflectivity rapidly decays along with stop of excitation light irradiation, is roughly regarded as a straight line on a double logarithmic chart, and may not always be limitedly set in the same span. This is because such a time span may be appropriately adjusted depending on states of the oxide semiconductor thin film to be measured.

The above-described "slow decay" is explained further in detail with reference to FIG. 1. FIG. 1 is a diagram illustrating an aspect of a variation in excess carrier density in the microwave photoconductive decay method. The vertical axis of FIG. 1 corresponds to reflectivity of a microwave. In the drawing, $T_0$ represents width of a pulse laser as excitation light. When an oxide semiconductor thin film sample is irradiated with excitation light, the excitation light is absorbed by the oxide semiconductor thin film, resulting in generation of excess carriers, i.e., excited carriers. At this time, as the excess carrier density increases, the annihilation rate of the carrier also increases. When the carrier injection rate becomes equal to the annihilation rate, the excess carrier density has a certain peak value. When the generation rate of the excess carriers becomes equal to the annihilation rate thereof, the excess carrier density saturates and maintains the certain value. If the excitation light irradiation is stopped in such a state, the number of the excess carriers decreases and returns to the value before start of the excitation light irradiation due to recombination and annihilation of the excess carriers, as generally known.

As illustrated in FIG. 1, while the reflectivity of the reflected wave from the oxide semiconductor thin film due to reflection of the microwave temporarily shows the maximum, the reflectivity rapidly decays along with stop of the irradiation of the excitation light. Such rapid decay is followed by a decay having a certain slope that roughly corresponds to the above-described "parameter corresponding to the slow decay observed after stopping the irradiation of the excitation light".

Specific examples of the slope include a slope of intensity of the reflected wave, i.e., reflectivity, to time in the above-described span, and a slope of a value obtained by logarithmic conversion of intensity of the reflected wave to a value obtained by logarithmic conversion of time in the span. In the embodiments described later, the B value in Formula (1) is used as the slope. As described before, the slope includes a slope in a region where the reflectivity slowly decays some time after stopping the irradiation of the excitation light.

The evaluation method of the invention is now described in detail. As described before, since the invention uses the microwave photoconductive decay method, the system usable in the invention must be able to irradiate excitation light and a microwave to the oxide semiconductor thin film as a sample, and detect intensity of a reflected microwave from the sample, the intensity being varied by the excitation light irradiation. Examples of such a system include a system illustrated in FIG. 13 described in detail later and a lifetime measurement system illustrated in FIG. 1 in PTL 2 described before. Since the lifetime measurement system is described in detail in PTL 2, such description should be seen. However, the system usable in the invention is not limited thereto.

A sample having the oxide semiconductor thin film thereon is first provided.

An amorphous oxide semiconductor thin film containing at least one element selected from the group consisting of In, Ga, Zn, and Sn is preferably used as the oxide semiconductor thin film. Such elements may be contained singly or in combination. Specific examples of such oxide include In oxide, In—Sn oxide, In—Zn oxide, In—Sn—Zn oxide, In—Ga oxide, Zn—Ga oxide, In—Ga—Zn oxide, and Zn oxide.

The oxide semiconductor thin film preferably has a thickness of about several tens to five hundreds of nanometers. The upper limit of the thickness is more preferably 200 nm or less, and most preferably 100 nm or less. The lower limit of the thickness is more preferably 10 nm or more, and most preferably 30 nm or more.

The sample usable in the invention includes the oxide semiconductor thin film provided on a substrate. The substrate includes various substrates typically used in the technical field of the invention, such as a glass substrate for a liquid crystal display having a thickness of about 0.7 mm and a size of several dozen square centimeters to more than several square meters called first to tenth generation.

Such a sample is irradiated with excitation light and a microwave.

As described with reference to FIG. 1, when the oxide semiconductor thin film sample is irradiated with irradiated excitation light, the excitation light is absorbed by the oxide semiconductor thin film and excess carriers are generated, and when the generation rate of the excess carrier becomes equal to the annihilation rate thereof, the excess carrier density saturates and maintains the certain value. If the excitation light irradiation is stopped in such a state, the number of the excess carriers decreases and returns to the value before start of the excitation light irradiation due to recombination and annihilation of the excess carriers.

In the invention, analysis of a variation in excess carrier density makes it possible to determine the carrier density of the oxide semiconductor thin film, and in turn evaluate the electrical resistivity, i.e., the sheet resistance or the specific resistance. This is probably due to the following reason.

The microwave applied to the oxide semiconductor thin film sample is reflected by plasma oscillation caused by carriers in the oxide semiconductor thin film. The reflectivity in such a case depends on the carrier density in the oxide semiconductor thin film. However, the number of carriers in the oxide semiconductor thin film in a steady state is not large enough to practically observe reflection of the microwave. However if the oxide semiconductor thin film is irradiated with the excitation light, excess carriers are generated in the film, and the reflectivity of the microwave is increased by plasma oscillation of the excess carriers. In addition, as the number of the excess carriers decreases along with stop of the excitation light irradiation, the reflectivity of the microwave also decreases.

Carriers in a silicon semiconductor or the like are typically caused by a shallow donor level below a conduction band in an energy band. In such a case, an energy level is about several tens of milli-electron volts below the conduction band, and thus most carriers are activated near room temperature. As generally known, carriers in the oxide semiconductor thin film in a steady state are also caused by a shallow donor level below a conduction band in an energy band. In the oxide semiconductor, however, the carrier level is relatively deep, about 0.1 to 0.2 eV. Hence, for the excess carriers generated by the excitation light irradiation, excited holes and electrons may be recombined, or the carriers may be re-emitted after being temporarily captured in the donor level. The ratio of such capture and reemission depends on the amount of the shallow donor level below the conduction band in the energy band. Hence, the annihilation process observed after stopping the excitation light is traced for the excess carriers caused by the excitation light irradiation, thereby influence of depth of the donor level can be analyzed. While the specific resistance of the oxide semiconductor thin film is represented by the product of charge, free electron, and mobility, the mobility of the oxide semiconductor thin film does not significantly vary as long as a composition of metal elements composing the oxide semiconductor thin film is the same. For example, the mobility of IGZO is about 10 $cm^2/VS$. Hence, a variation in reflectivity of the microwave, i.e., a variation in excess carrier density, observed by the microwave photoconductive decay method roughly correlates with each of the carrier concentration and the electrical resistivity.

Amorphous semiconductor materials such as an oxide semiconductor include a material having continuous levels between a conduction band and a donor level, such as amorphous silicon and IGZO. In such a case, an annihilation process of carriers observed by the microwave photoconductive decay method can be understood as superimposition of individual carrier transition behaviors between the energy levels. As a result, the decay process is observed over a somewhat long time span compared with transition between two energy levels. The time dependence of such decay follows a power law relationship with respect to time.

Hence, after the first step, the parameter corresponding to the slow decay observed in a time span over a range roughly from 0.1 to 10 µs is calculated, thereby the carrier density of the oxide semiconductor thin film can be determined. As a result, the electrical resistivity such as sheet resistance or specific resistance can be evaluated.

Hereinbefore, the evaluation method of the oxide semiconductor thin film of the invention has been described in detail.

The invention includes a method for performing quality control of the oxide semiconductor thin film through applying the evaluation method to one of steps of a semiconductor manufacturing process. The evaluation method is thus applied to one of the steps of the semiconductor manufacturing process, thereby film quality can be controlled through feeding back the evaluation results of the electrical resistivity of the oxide semiconductor thin film, i.e., the sheet resistance or the specific resistance, to adjust a manufacturing condition. Hence, quality control of the oxide semiconductor can be appropriately performed.

The above-described "one of steps" means an appropriate step in a semiconductor manufacturing process. The investigation results of the inventors have revealed that manufacturing steps having influence on stress tolerance include (1) a formation step of the gate insulating film, (2) a formation step of the oxide semiconductor thin film, (3) a heat treatment (hereinafter, also referred to as pre-anneal treatment) step after formation of the oxide semiconductor thin film, and (4) a formation step of a passivation film that may be provided on the surface of the oxide semiconductor thin film. For example, when the evaluation method is applied to one of such steps, the quality of the oxide semiconductor thin film can be accurately controlled.

The passivation film (hereinafter, also referred to as passivation insulating film) includes a passivation film (hereinafter, also referred to as etch stop layer) and a passivation film (hereinafter, also referred to as final passivation film) that further protects the surface of that passivation film.

Specifically, the oxide semiconductor thin film may be formed on the gate insulating film that has been formed on a substrate, or may be directly formed on the substrate without forming the gate insulating film immediately before performing the evaluation method. Alternatively, the evaluation method may be performed after the oxide semiconductor thin film formed on the substrate or the gate insulating film is subjected to the pre-anneal treatment using, for example, oxygen or water vapor, or may be performed before formation of the passivation insulating film. Furthermore, the evaluation method may be performed at one point in one step of the manufacturing process or at several points in two or more steps. Applying the evaluation method of the invention to the two or more steps as in the latter case allows measurement of in-plane distribution, i.e., in-plane variations in sheet resistance or specific resistance of the oxide semiconductor thin film.

For example, the evaluation method of the invention can be applied to one of the cases of forming the oxide semiconductor thin film on a substrate; forming the oxide semiconductor thin film on the gate insulating film that has been formed on the substrate; performing the pre-anneal treatment after forming the oxide semiconductor thin film, where the gate insulating film may be or may not be formed before forming the oxide semiconductor thin film; forming the passivation film on the formed oxide semiconductor thin film following one of the above described cases, the passivation film including the final passivation film for further protecting that passivation film; and performing heat treatment (hereinafter, also referred to as post anneal) after forming the passivation film.

The evaluation method of the invention makes it possible to easily, shortly, and inexpensively evaluate the stress tolerance of each of oxide semiconductor thin films having various compositions or concentrations in a stage of developing a material for the oxide semiconductor thin film. Furthermore, the evaluation method of the invention makes it possible to perform in-line evaluation of the electrical properties of the oxide semiconductor thin film in a short time and in a noncontact manner in a manufacturing line of a liquid crystal display or the like, which improves productivity such as a production yield, leading to appropriate quality control of the oxide semiconductor.

The invention includes an evaluation element used in one of the above-described evaluation methods. The evaluation element includes the oxide semiconductor thin film provided on a substrate, and has a configuration corresponding to the above-described one of steps typified by the steps (1) to (4).

Figure 8:
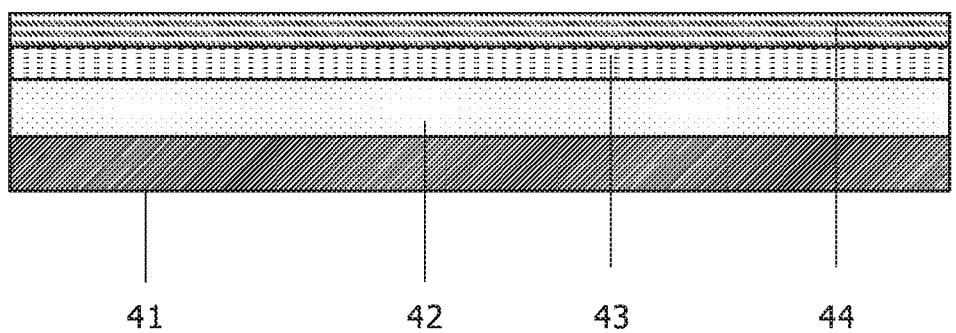
FIG. 8 is a schematic diagram illustrating another exemplary configuration of the evaluation element according to the invention.

Specific examples of the evaluation element include (a) an evaluation element including the oxide semiconductor thin film directly provided on the surface of the substrate; (b) an evaluation element including the oxide semiconductor thin film directly provided on the surface of the gate insulating film; and (c) an evaluation element including the passivation film such as, for example, the etch stop layer shown in FIG. 8 provided on the surface of the oxide semiconductor thin film in the above (a) or (b) and the final passivation film shown in FIG. 6.

The evaluation element of the invention importantly includes the oxide semiconductor thin film that is directly provided on the surface of the substrate or the gate insulating film as described in the above (a) or (b). In other words, a metal electrode such as a gate electrode does not exist directly below the oxide semiconductor thin film. This is because if the gate electrode or the like exists directly below the oxide semiconductor thin film, since the number of electrons as free carriers of the gate electrode is large, $10^{18}$ cm$^{-3}$ or more, the gate electrode has a dominant influence on the reflectivity of the microwave.

FIGS. 3 to 9 illustrate an exemplary configuration of the evaluation element according to the invention. As illustrated in FIGS. 3 to 9, no metal electrode is provided directly below the oxide semiconductor thin film.

Figure 3:
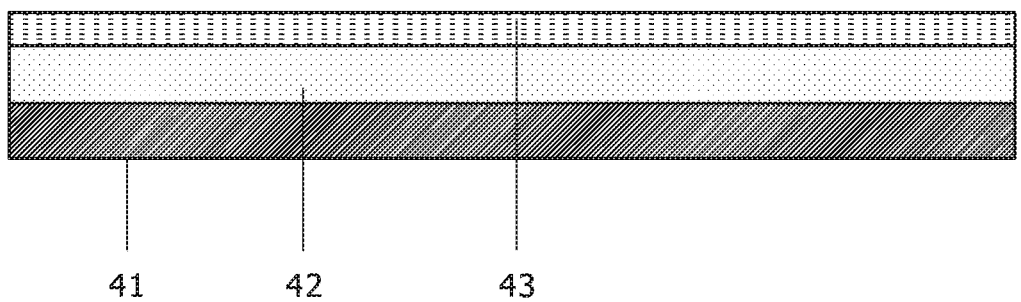
FIG. 3 is a schematic diagram illustrating an exemplary configuration of an evaluation element according to the invention.

In the drawings, for example, FIG. 3 shows a configuration where a gate insulating film 42 and an oxide semiconductor layer 43 are provided in this order on a substrate such as a glass substrate 41. The oxide semiconductor thin film is not patterned.

Figure 4:
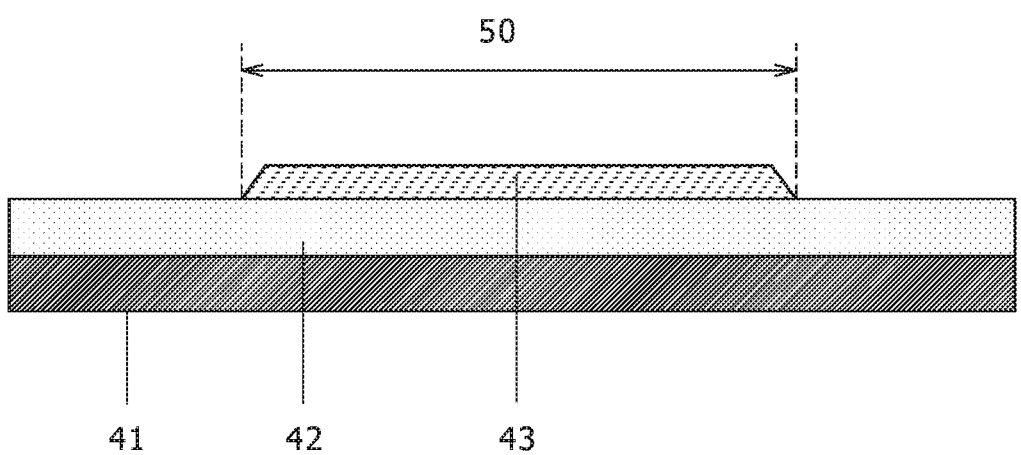
FIG. 4 is a schematic diagram illustrating another exemplary configuration of the evaluation element according to the invention.

In FIG. 4, the gate insulating film 42 and the oxide semiconductor layer 43 are provided in this order on the substrate such as the glass substrate 41, and then the oxide semiconductor layer 43 is patterned.

Figure 5:
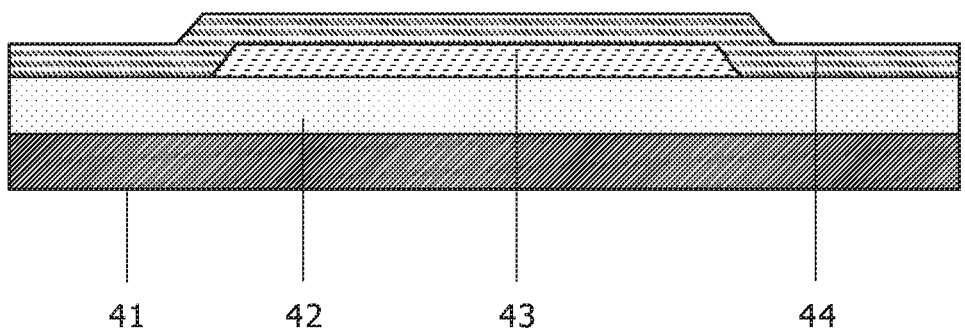
FIG. 5 is a schematic diagram illustrating another exemplary configuration of the evaluation element according to the invention.

In FIG. 5, the gate insulating film 42, the patterned oxide semiconductor layer 43, and an etch stop layer 44 as a patterned passivation film are provided in this order on the substrate such as the glass substrate 41.

Figure 6:
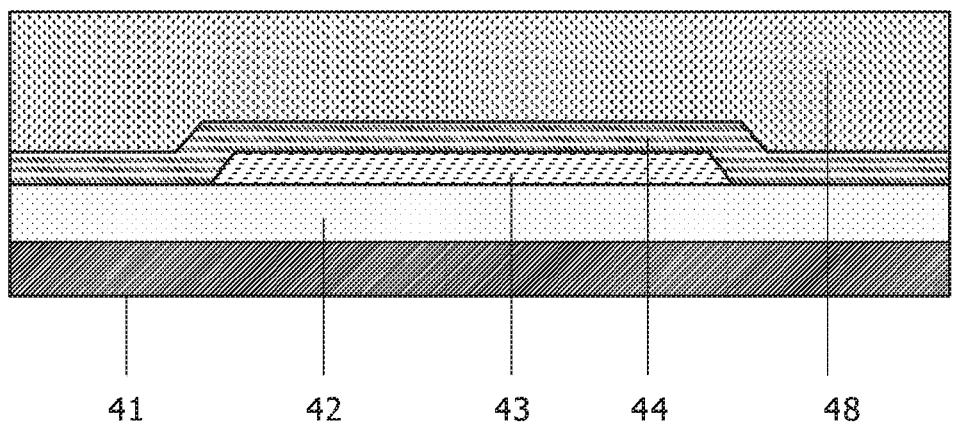
FIG. 6 is a schematic diagram illustrating another exemplary configuration of the evaluation element according to the invention.

In FIG. 6, the gate insulating film 42, the patterned oxide semiconductor layer 43, the etch stop layer 44 as a patterned passivation film, and a final passivation film 48 are provided in this order on the substrate such as the glass substrate 41.

Figure 7:
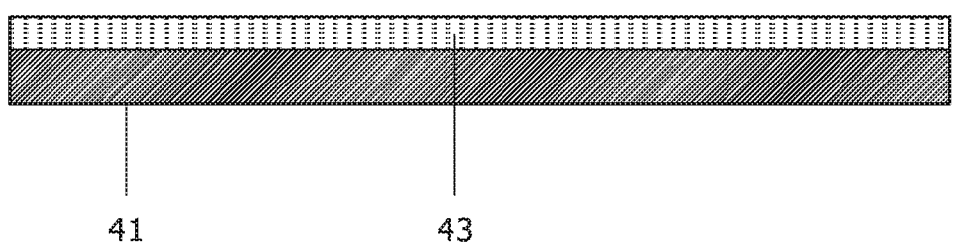
FIG. 7 is a schematic diagram illustrating another exemplary configuration of the evaluation element according to the invention.

In FIG. 7, the semiconductor layer 43 is provided on the substrate such as the glass substrate 41.

In FIG. 8, the gate insulating film 42, the patterned oxide semiconductor layer 43, and the etch stop layer 44 as a passivation film are provided in this order on the substrate such as the glass substrate 41.

Figure 9:
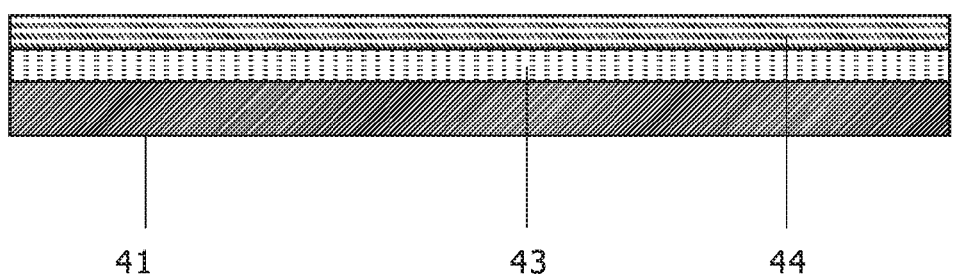
FIG. 9 is a schematic diagram illustrating another exemplary configuration of the evaluation element according to the invention.

In FIG. 9, the oxide semiconductor layer 43 and the etch stop layer 44 as a passivation film are provided in this order on the substrate such as the glass substrate 41.

Furthermore, the invention includes an evaluation device including a plurality of evaluation elements disposed on a substrate, each evaluation element being one of the above-described evaluation elements.

Figure 10:
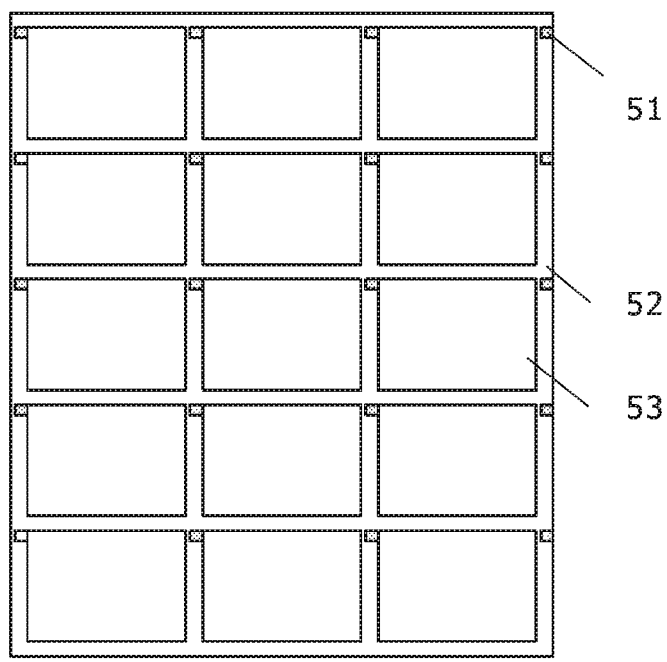
FIG. 10 is a schematic diagram illustrating an exemplary configuration of an evaluation device according to the invention.

FIG. 10 is a schematic diagram illustrating an exemplary configuration of such an evaluation device. As illustrated in FIG. 10, a plurality of evaluation elements 51 are regularly arranged on a glass substrate 52 to be used in a mass production line. Such an evaluation device allows quality control of the oxide semiconductor thin film. Specifically, the evaluation device allows measurement of distribution in a substrate plane, i.e., in-plane variations in electrical resistivity, and allows measurement of distribution between substrates, i.e., variations in electrical resistivity between substrates.

Embodiments of the invention are now described in detail with reference to drawings. However, the evaluation system of the invention is not limited to the following configuration, and may be appropriately modified or altered.

Figure 13:
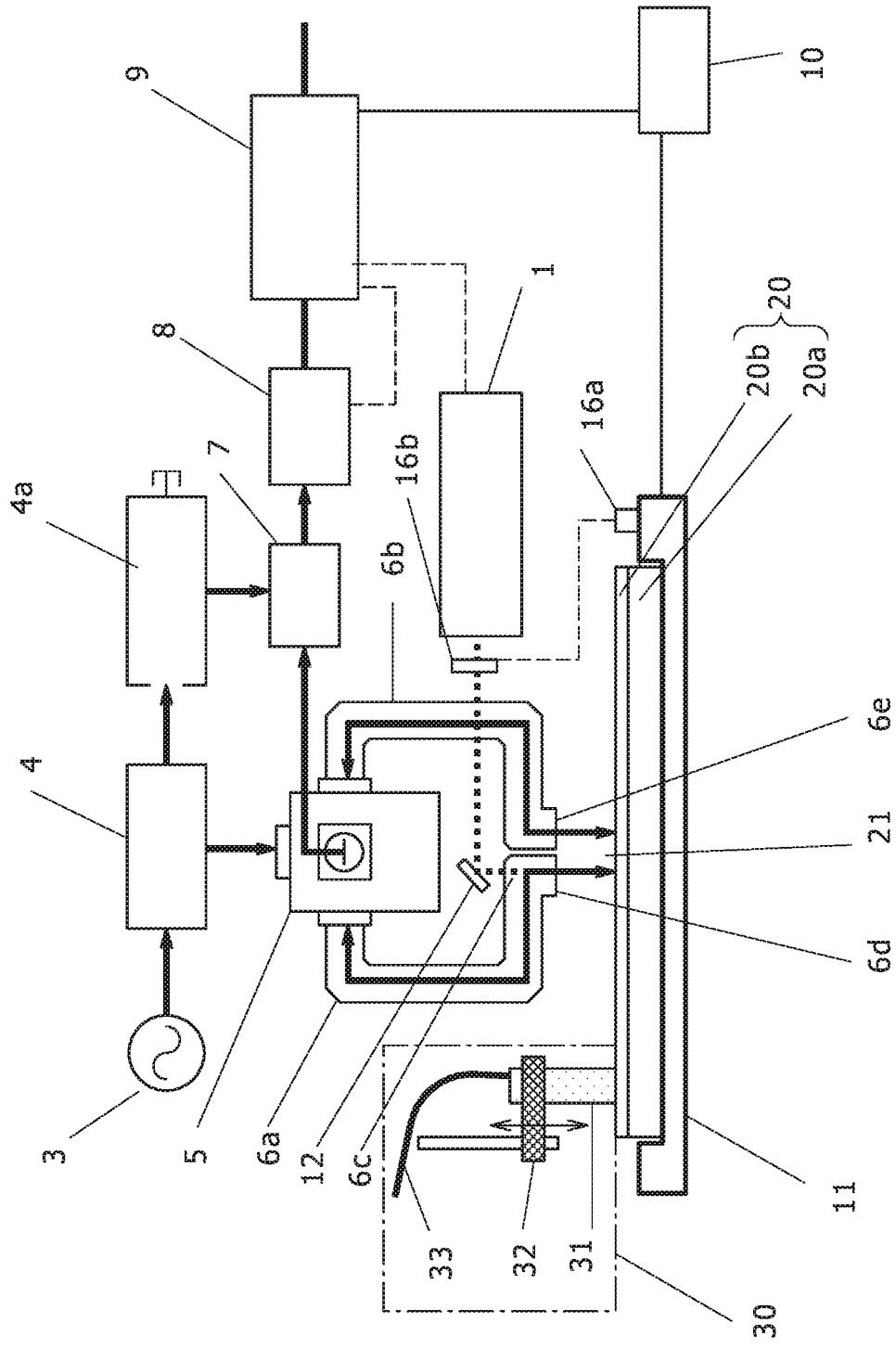
FIG. 13 is a schematic illustration illustrating an exemplary evaluation system according to the invention.

FIG. 13 is a schematic illustration illustrating an exemplary configuration of a system used in the evaluation method of the oxide semiconductor thin film. The evaluation system illustrated in FIG. 13 includes an excitation light irradiation unit 1 that irradiates a measurement site of a sample 20 including an oxide semiconductor thin film 20b provided on a substrate 20a with excitation light to generate electron-hole pairs in the oxide semiconductor thin film, a microwave irradiation unit 3 that irradiates the measurement site of the sample 20 with a microwave, a reflected microwave intensity detection unit 7 that detects intensity of a reflected microwave from the sample 20 due to reflection of the microwave, the intensity being varied by the excitation light irradiation, and an unit to evaluate the electrical resistivity of the sample 20 based on the detection data of the reflected microwave intensity detection unit. This configuration makes it possible to measure and evaluate a variation in reflectivity and the electrical resistivity by one system.

The excitation light irradiation unit 1 has a light source that outputs excitation light to be applied to the sample 20, and generates electron-hole pairs in the oxide semiconductor thin film through excitation light irradiation. The excitation light irradiation unit 1 preferably has a light source that outputs excitation light having energy equal to or larger than the bandgap of the oxide semiconductor thin film. The light source effectively generates carriers through outputting the energy equal to or larger than the bandgap of the oxide semiconductor thin film, which preferably leads to sensitive measurement. The excitation light irradiation unit 1 should include an ultraviolet laser as the light source, for example. Specifically, the ultraviolet laser includes a semiconductor laser such as a pulsed laser that emits, as the excitation light, pulsed ultraviolet light having a wavelength of 349 nm, power of 1 µJ/pulse, a pulse width of about 15 ns, and a beam diameter of about 1.5 mm, for example, a third harmonic of a YLF laser.

The excitation light irradiation unit 1 receives a timing signal transmitted from an evaluation unit 9 (as shown by a broken line in the drawing), and outputs the excitation light (hereinafter, the meaning of the excitation light includes "pulsed light") with the reception of the timing signal as a trigger. The timing signal is transmitted to a signal processor 8 at the same time. The excitation light can be output from the excitation light irradiation unit 1 while being adjusted in output power by an output adjustment power monitor 16a and an output adjustment unit 16b.

The excitation light output from the excitation light irradiation unit 1 is reflected by an optical path change unit (hereinafter, also referred to as mirror) such as a mirror, and is condensed by a condensing unit (hereinafter, also referred to as condensing lens) such as a condensing lens, passes through a small opening 6c provided in a first waveguide 6a, and is applied to a measurement site having a diameter of, for example, about 5 to 10 µm of the sample 20 through an opening 6d located at an end close to the sample 20 of the first waveguide 6a. In this way, the mirror 12 and the condensing lens condense the excitation light output from the excitation light irradiation unit 1, and guide the excitation light to the measurement site of the sample 20. Consequently, excited carriers are generated in a small excitation light irradiation region 21 as the measurement site of the sample 20.

The microwave irradiation unit 3 outputs a microwave to be applied to the measurement site of the sample 20. Examples of the microwave irradiation unit 3 include a microwave oscillator such as a Gunn diode resonating at a frequency of 26 GHz.

A directional coupler 4 bifurcates the microwave output from the microwave irradiation unit 3. One of the bifurcated output waves (hereinafter, referred to as first microwave Op1) is transmitted to a magic T (5) side, while the other bifurcated output wave (hereinafter, referred to as second microwave Op2) is transmitted to a LO input terminal of the reflected microwave intensity detection unit 7 via a phase regulator 4a. The directional coupler 4 is a 10 dB coupler, for example.

The magic T (5) bifurcates the first microwave Op1, and outputs a difference signal Rt1 (hereinafter, also referred to as reflected-wave difference signal) and a sum signal between the reflected waves caused by reflection of the bifurcated, first microwaves on the sample 20.

One of the microwaves Op1 bifurcated by the magic T (5) (hereinafter, also referred to as first main microwave Op11) is guided to the measurement site including an excited portion of the sample 20 by the first waveguide 6a connected to the magic T (5), and is radiated from the opening 6d at an end of the first waveguide 6a. Consequently, the first main microwave Op11 is applied to the measurement site of the sample 20. Furthermore, the first waveguide 6a serves as an antenna (hereinafter, also referred to as waveguide antenna) radiating the first main microwave Op11, and serves to capture the reflected wave of the first main microwave Op11, which is applied to the measurement site, by the opening 6d at the end of the first waveguide 6a, and guide back the captured reflected wave to the magic T (5).

The other of the first microwaves Op1 bifurcated by the magic T (5) (hereinafter, also referred to as first sub microwave Op12) is guided to the vicinity of the measurement site of the sample 20a, i.e., a portion containing no excited region by the excitation light, by a second waveguide 6b connected to the magic T (5), and is radiated from an opening 6e at an end of the second waveguide 6b. Consequently, the first sub microwave Op12 is applied to the vicinity of the measurement site of the sample 20a. Furthermore, the second waveguide 6b serves as a waveguide antenna radiating the first sub microwave Op12, and serves to capture the reflected wave of the first sub microwave Op12, which is applied to the vicinity of the measurement site, by the opening 6e at the end of the second waveguide 6b, and guide back the captured reflected wave to the magic T (5). The path length along which the first waveguide 6a guides the microwave is equal to the path length along which the second waveguide 6b guides the microwave.

A difference signal between the two reflected waves guided to the magic T (5) by the first waveguide 6a and the second waveguide 6b, i.e., a difference signal between reflected waves caused by reflection of the bifurcated, first microwaves Op11 and Op12 on the sample 20, that is, a reflected-wave difference signal Rt1 is output by the magic T (5), and transmitted to an RF input terminal of the reflected microwave intensity detection unit 7.

The reflected microwave intensity detection unit 7 mixes the second microwave Opt and the reflected-wave difference signal Rt1, and thus outputs a detection signal Sg1. The detection signal Sg1 indicates an example of intensity of the reflected-wave difference signal Rt1, for example, intensity of the reflected wave of the first microwave Op1 applied to the sample 20, and is fed to the signal processor 8. The intensity of the reflected-wave difference signal Rt1 is varied by excitation light irradiation to the sample 20 held at a predetermined position by a substrate holder. In this way, the reflected microwave intensity detection unit 7 detects the intensity of the reflected-wave difference signal Rt1. A mixer or a microwave detector (hereinafter, also referred to as detector), which receives a microwave and outputs an electric signal, i.e., a current or a voltage, corresponding to the intensity of the microwave, may be provided as the reflected microwave intensity detection unit 7.

The intensity of the reflected-wave difference signal Rt1 detected by the reflected microwave intensity detection unit 7 is varied by excitation light irradiation to the measurement site of the sample 20. Specifically, the intensity of the reflected-wave difference signal Rt1 is temporarily increased by the excitation light irradiation and then decays. As the measurement site has more impurities or defects, a peak value of the intensity of the reflected-wave difference signal Rt1 becomes smaller, and the decay time of the intensity, i.e., carrier lifetime also becomes shorter.

For the intensity of the reflected-wave difference signal Rt1, the intensity being varied by excitation light (pulsed light) irradiation, a parameter corresponding to the slow decay, which is observed after stopping the excitation light irradiation after the peak value of the intensity appears, is an index for evaluating the electrical resistivity of the sample 20.

The signal processor 8 detects a peak value Sp of a variation in intensity of the reflected-wave difference signal Rt1 detected by the reflected microwave intensity detection unit 7, and transmits the detection result to the evaluation unit 9. More specifically, the signal processor 8 receives a timing signal from the evaluation unit 9, and monitors a variation in the reflected-wave difference signal Rt1 for a predetermined time with the reception of the timing signal as a trigger, and detects the maximum of a level of the reflected-wave difference signal Rt1 obtained during such monitoring as the peak value Sp of the variation in intensity of the reflected-wave difference signal Rt1. The signal processor 8 has a delay circuit that performs delay processing on the reflected-wave difference signal Rt1, sequentially detects signal intensity of the delay-processed signal at a predetermined sampling frequency, and detects the peak value Sp of the variation in intensity of the reflected-wave difference signal Rt1 from variations between the detected values.

A computer including CPU, a storage, and an input-output signal interface can be used as the evaluation unit 9, in which the CPU executes a predetermined program so that the computer performs various types of processing.

For example, the evaluation unit 9 outputs a timing signal indicating output timing of the excitation light to the excitation light irradiation unit 1 and the signal processor 8, and captures the peak value Sp of the reflected-wave difference signal Rt1 detected by the signal processor 8 and stores the peak value Sp in the storage of the evaluation unit 9. The reflected-wave difference signal Rt1 as the stored detection data is used for evaluation of the electrical resistivity of the sample 20.

A stage controller 10 controls an X-Y stage 11 according to an instruction from the evaluation unit 9, and thus performs positioning control of the measurement site of the sample 20.

An undepicted sample stage is provided over the X-Y stage 11. The sample stage is a plate-like component including a metal such as aluminum, stainless steel, or iron, or another conductor. An undepicted substrate holder is provided over the sample stage, and the sample 20 is placed on the substrate holder. Consequently, the sample stage is disposed on a side opposite to a side on which the sample 20 is irradiated with the first microwaves Op11 and Op12, i.e., disposed on a side lower than the sample 20.

The substrate holder is a solid dielectric fixed onto the sample stage. The substrate holder is the solid dielectric inserted between the substrate and the sample stage, and is composed of a material that is a dielectric having a relatively large refractive index, such as glass or ceramics. This shortens the wavelength of the microwave using the substrate holder as a medium, so that a relatively thin and light substrate holder can be used.

As described above, according to the configuration for evaluating the electrical resistivity of the invention, photo-excited carriers are generated in the oxide semiconductor thin film by the excitation light output from the excitation light irradiation unit 1, and the photoexcited carriers move by an electric field of the microwave output from the microwave irradiation unit 3. The kinetic state of the photoexcited carriers is affected by impurities, defects, and the like in the semiconductor. Hence, intensity of the reflected microwave from the sample is detected by the reflected microwave intensity detection unit 7, and a variation in excess carrier concentration is analyzed by the evaluation unit 9 as described before, which allows determination of the carrier concentration in the oxide semiconductor thin film and evaluation of the electrical resistivity. During this operation, the evaluation unit 9 controls a position of a stage including an X-Y table 11, allowing mapping measurement for determining the electrical resistivity in a predetermined range.

Furthermore, the evaluation system having an electrical resistance measurement unit makes it possible to provide a system not only performing evaluation of the electrical resistivity, but also performing, in a short time, in-line evaluation of the electrical properties of the oxide semiconductor thin film. In the above-described evaluation of the electrical resistivity, the electrical resistivity is evaluated based on the so-called slow decay. Through investigations, the inventors have found that the slow decay is caused by film defects in the oxide semiconductor thin film. Hence, the electrical resistivity, which is measured and evaluated according to the microwave photoconductive decay method, is also varied depending on the number of the film defects.

The electrical resistivity of the oxide semiconductor thin film may be varied due to contamination or impurities even in the same plane, and thus has different values depending on measurement points. To perform appropriate quality control of the oxide semiconductor thin film, therefore, it is important that a microwave photoconduction measurement point for evaluating film defects in the oxide semiconductor thin film is substantially equal to an electrical resistivity measurement point for evaluating film surface defects.

Hence, if the evaluation system has an electrical resistance measurement unit, such measurements can be easily and accurately performed at substantially the same point only by appropriately moving the X-Y stage. Hence, if the evaluation system having the electrical resistance measurement unit is used in a manufacturing line for a liquid crystal display or the like, productivity is significantly improved, and further appropriate quality control of the oxide semiconductor thin film can be performed.

A configuration of the system having the electrical resistance measurement unit is described with reference to FIG. 13. While the system of FIG. 13 measures and evaluates the variation in reflectivity and the electrical resistivity according to the microwave photoconductive decay method as described above, the system further has an electrical resistance measurement unit 30. Although a mounting position of the electrical resistance measurement unit 30 is not specifically limited, the electrical resistance measurement unit 30 is desirably mounted such that the electrical resistivity can be measured at roughly the same point as the microwave photoconduction measurement point of the oxide semiconductor thin film by moving the X-Y stage 11 as described above. The electrical resistance measurement unit 30 preferably includes an electrical resistivity measurement head 31 and an up-and-down unit 32 for the electrical resistivity measurement head 31. The electrical resistance measurement unit 30 can measure the electrical resistivity of the sample 20.

The electrical resistivity measurement head 31 includes a resistivity measurement unit corresponding to a resistance value, such as a measurement probe including a double ring electrode, and can measure the electrical resistivity of the sample 20 by a measurement method in accordance with JIS K6911. The electrical resistivity measurement head 31 includes four needle electrodes arranged on a straight line, and can perform resistance measurement by a four probe method in accordance with JIS K7194.

The up-and-down unit 32 of the electrical resistivity measurement head 31 is an up-and-down mechanism that lowers the electrical resistivity measurement head to a desired position for measurement of the electrical resistivity of the sample 20. Various known electrical resistivity meters are usable as an unit configured to measure the electrical resistivity. When an electrical resistance meter such as Hiresta from Mitsubishi Chemical Analytech Co., Ltd. is used, a probe corresponding to the electrical resistivity measurement head 31 should be lowered by the up-and-down unit 32 so as to come into contact with the surface of the sample 20, and be then raised so as to be released from contact with the sample 20. The measured electrical resistivity can be sent for evaluation to an evaluation unit, for example, having a configuration similar to that of the evaluation unit 9 through a measured-value transmission line 33. In addition, the resistivity can be evaluated by an electrical resistance meter such as a probe head from JANDAL.

This application claims the benefit of Japanese Priority Patent Applications JP 2013-250412 filed on Dec. 3, 2013 and JP 2014-104629 filed on May 20, 2014, the entire contents of each of which are incorporated herein by reference.

EMBODIMENTS

Although the invention is now described in detail with some embodiments, the invention should not be limited thereto, and modifications or alterations thereof may be made within the scope without departing from the gist described before and later, all of which are included in the technical scope of the invention.

First Embodiment

In a first embodiment, the following experiment was conducted to evaluate a correlation between a parameter of each of oxide semiconductor thin films, which are InGaZnO and IGZO herein, the parameter being calculated according to the microwave photoconductive decay method, and a sheet resistance value.
(1) Sample Preparation EAGLE XG from Corning having a diameter of 100 mm and a thickness of 0.7 mm was provided as a glass substrate. IGZO as an oxide semiconductor thin film was deposited on the glass substrate by a sputtering process under the following condition. In the first embodiment, the additive amount of oxygen was varied during the sputtering to vary film quality of the oxide semiconductor thin film.

Sputtering apparatus: CS-200 from ULVAC, Inc.
Sputtering target composition: InGaZnO$_4$ (In:Ga:Zn=1:1:1 in atomic ratio)
Substrate temperature: Room temperature
Thickness of oxide semiconductor layer: 200 nm
Additive amount of oxygen: O$_2$/(Ar+O$_2$)=0%, 4%, 8%, 12%, 16%, and 20% in volume ratio
Gas pressure: 1 mTorr Subsequently, a condition of pre-anneal treatment, specifically pre-anneal time, is varied to prepare various samples in order to improve film quality of the oxide semiconductor thin film, i.e., improve the TFT characteristics such as mobility, switching performance, and stability of the characteristics during operation. Specifically, in the pre-anneal treatment condition, while pre-anneal temperature was fixed to 350° C. in the atmosphere, pre-anneal time was varied from 0 min (not treated), to 5 min, to 30 min, to 60 min, to 120 min, so that various samples were produced.

Each of the samples produced in this way was subjected to determination of "parameter corresponding to slow decay observed after excitation light irradiation" of the microwave photoconductive decay method. Specifically, the microwave photoconductive decay method was performed under the following condition using an evaluator having a configuration as illustrated in FIG. 1 of PTL 2 (specifically, LTA-1820SP from Kobelco Research Institute, Inc.), so that variations in reflectivity were measured.

Laser wavelength: 349 nm ultraviolet light
Pulse width: 15 ns
Pulse energy: 1 µJ/pulse
Beam diameter: 1.5 mmφ
Number of pulses for each measurement=64 shots
Evaluator: LTA-1820SP from Kobelco Research Institute, Inc.

Such samples were separately subjected to measurement of sheet resistance using Hiresta from Mitsubishi Chemical Analytech Co., Ltd. The sheet resistance was measured to evaluate a correlation between the electrical resistivity evaluated by the microwave photoconductive decay method and actually measured values of the sheet resistance.

Figure 11:
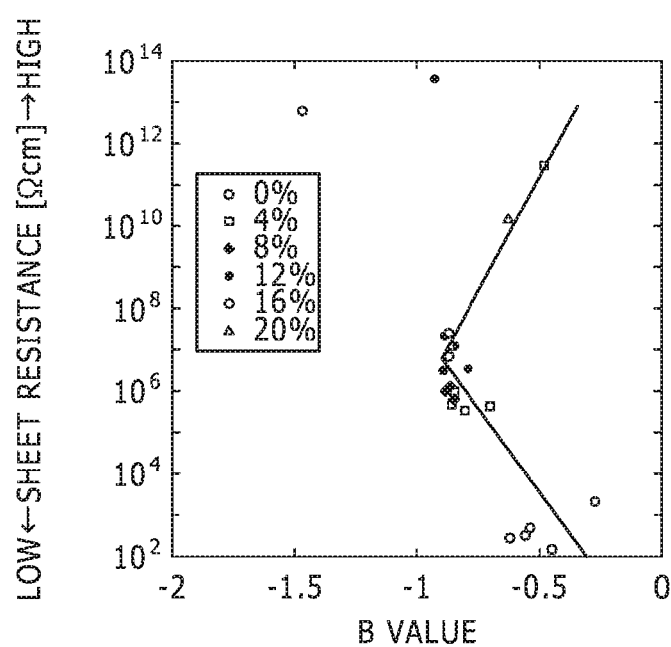
FIG. 11 is a chart illustrating a relationship between a B value in Formula (1) and a sheet resistance in the first embodiment.

FIG. 11 shows results of the measurement according to the microwave photoconductive decay method. In the drawing, the vertical axis represents sheet resistance, and the horizontal axis represents a parameter calculated based on a relationship between reflectivity and measurement time obtained by the microwave photoconductive decay method, i.e., "parameter corresponding to slow decay" defined in the invention. In detail, the parameter corresponds to the B value (slope) in Formula (1) representing the relationship between reflectivity and measurement time. In the first embodiment, a slope (−B) in the above-described measurement time span was calculated for measurement time x=0.5 to 2.5 µs.

[Numerical formula 1]

$$y = Ax^{-B} \qquad (1)$$

where x is measurement time, and y is reflectivity.

FIG. 11 reveals that the sheet resistance correlates with the B value. In detail, as the sheet resistance increases from $10^2$ to $10^7$, the B value (absolute value) also increases. For the sheet resistance of more than $10^7$, however, the B value (absolute value) decreases with a further increase in the sheet resistance. FIG. 11 further reveals that the B value (absolute value) is affected by the additive amount of oxygen during the sputtering and by the pre-anneal time.

Through the basic experiment, the inventors have found that the B value (absolute value) increases and converges to one point through optimizing each of various treatments. In addition, the inventors have found that when the B value is similar to the converged value, good TFT characteristics are given. Hence, when conditions such as the additive amount of oxygen during sputtering and the pre-anneal time are each appropriately adjusted such that the B value has a maximum, good TFT characteristics are promisingly exhibited.

Second Embodiment

In a second embodiment, the following experiment was conducted to evaluate a correlation between a parameter of each of oxide semiconductor thin films, which are InGaZnO and IGZO herein, the parameter being calculated according to the microwave photoconductive decay method, and a specific resistance value.
(1) Sample Preparation IGZO as an oxide semiconductor thin film was deposited by a sputtering process under the following condition on a glass substrate (EAGLE XG from Corning 100 mm in diameter and 0.7 mm in thickness).

Sputtering apparatus: SMD-450 from ULVAC, Inc.
Sputtering target composition: InGaZnO$_4$ (In:Ga:Zn=1:1:1 in atomic ratio)
Substrate temperature: Room temperature
Thickness of oxide semiconductor layer: 40 nm
Additive amount of oxygen: O$_2$/(Ar+O$_2$)=4% in volume ratio
Gas pressure: 1 mTorr Subsequently, each sample was heat-treated in the atmosphere for a pre-anneal time of 60 min at a pre-anneal temperature of 350° C. Each of the samples produced in this way was subjected to determination of "parameter corresponding to slow decay observed after excitation light irradiation" of the microwave photoconductive decay method at appropriate measurement points on the substrate, specifically 21 measurement points in total disposed at equal intervals. The measurement condition of the microwave photoconductive decay method was the same as that in the first embodiment, and the B value was used as the parameter. In the second embodiment, however, the slope, i.e., the B value was determined while the measurement time x in Formula (1) is varied as follows: 0.5 to 1.5 µs, 0.5 to 1 µs, 1 to 1.5 µs, and 1.5 to 2 µs.

Such samples were separately subjected to measurement of specific resistance using Hiresta from Mitsubishi Chemical Analytech Co., Ltd. The specific resistance was measured to evaluate a correlation between the electrical resistivity evaluated by the microwave photoconductive decay method and actually measured values of the specific resistance.

Figure 12A:
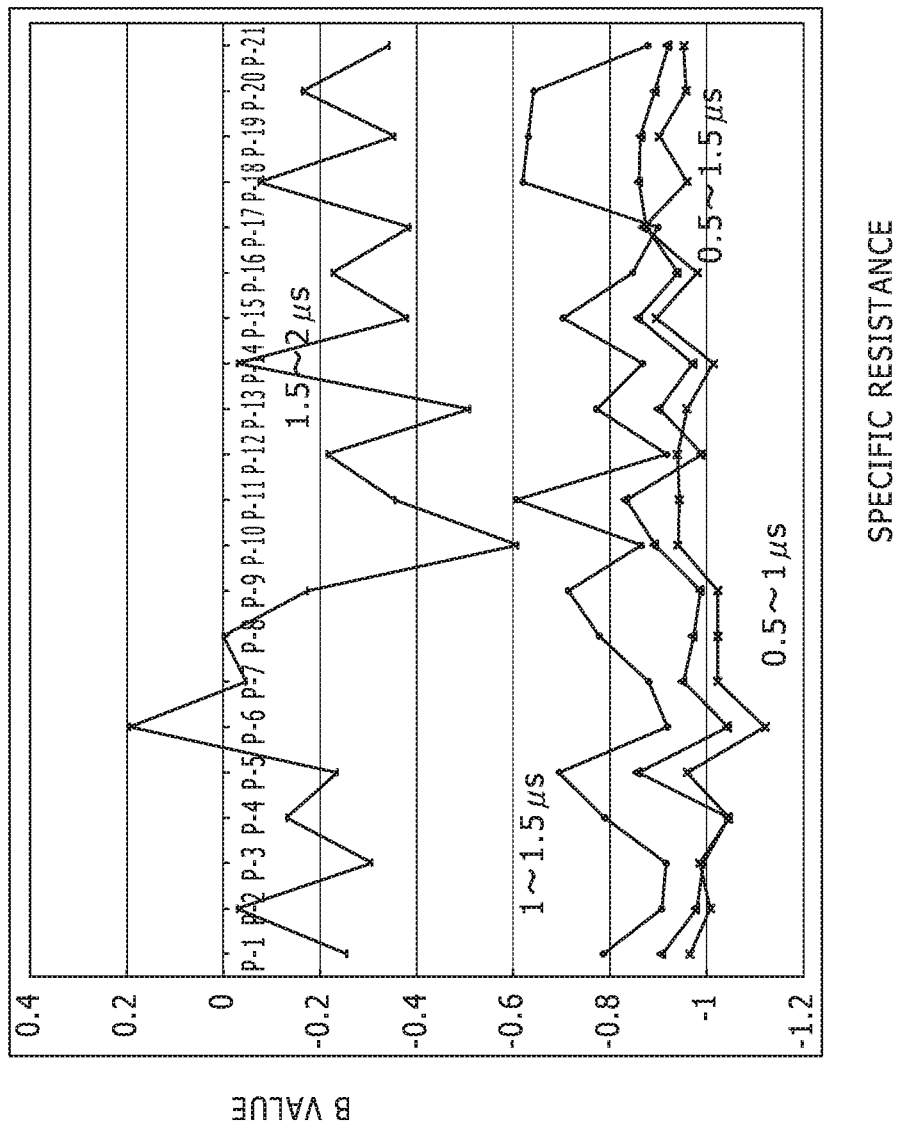
FIG. 12A is a chart illustrating results of the second embodiment, showing a relationship between a specific resistance at each measurement point on a substrate and the B value in Formula (1).

FIG. 12A shows results of the measurement. In the drawing, the horizontal axis corresponds to measurement points P-1 to P-21, and the vertical axis represents the B value at each measurement point. The vertical axis is graduated in 0.2 from −1.2 to 0.4.

As shown in FIG. 12A, while a variation in the B value with respect to the specific resistance at each measurement point is small for the measurement time x=0.5 to 1 μs or 0.5 to 1.5 μs, the variation is significant for the measurement time x=1 to 1.5 μs, and more significant for the measurement time x=1.5 to 2 μs.

Furthermore, a correlation coefficient between Formula (1) and a measured decay waveform of the reflectivity of the microwave was obtained as a virtual function for calculation of the B value obtained in the above. A value of the correlation coefficient closer to 1 shows a stronger correlation between Formula (1) and a measured value of the decay waveform, specifically more accurate fitting. In other words, the calculated B value is shown to be more appropriate as a characterization parameter of the oxide semiconductor thin film. The value closer to zero (0) shows a weaker correlation between Formula (1) and the measured value of the decay waveform, specifically less accurate fitting. In other words, the calculated B value is shown to be inappropriate as a characterization parameter of the oxide semiconductor thin film. In FIG. 12B, the horizontal axis corresponds to the measurement points P-1 to P-21, and the vertical axis represents the correlation coefficient. The vertical axis is graduated in 0.1 from 0 to 1.

As shown in FIG. 12B, while the correlation coefficient at each measurement point is roughly 1 for the measurement time x=0.5 to 1 μs or 0.5 to 1.5 μs, the correlation coefficient decreases to the neighborhood of about 0.5 to 0.8 for the measurement time x=1 to 1.5 μs, and decreases to roughly 0 for the measurement time x=1.5 to 2 μs. This means that the correlation deviates from a linear relationship due to noise during the measurement. Such results agree with the results shown in FIG. 12A. Specifically, while the correlation coefficient in FIG. 12B is roughly 1 in the small variation region of x=0.5 to 1.5 μs in FIG. 12A, the correlation coefficient in FIG. 12B is roughly 0 in the large variation region of x=1.5 to 2 μs in FIG. 12A.

These results prove that under the condition of this experiment, if the B value as a slope for the measurement time x=0.5 to 1.5 μs is used as "parameter corresponding to slow decay" defined in the invention, the specific resistance of the oxide semiconductor thin film can be evaluated indirectly and accurately.

The slow decay calculated according to the microwave photoconductive decay method was confirmed to correlate with the sheet resistance or the specific resistance of the oxide semiconductor thin film through comparison with Hiresta.

Third Embodiment

The B value analysis was performed by the microwave photoconductive decay measurement method using an evaluator including the microwave photoconductive decay method evaluator (LTA-1820SP from Kobelco Research Institute, Inc.) incorporating the electrical resistance meter (Hiresta from Mitsubishi Chemical Analytech Co., Ltd.) as with the second embodiment, and the specific resistance was measured with the electrical resistance meter.

Specifically, a system, which has a configuration illustrated in FIG. 13 but includes a microwave photoconductive decay method evaluator (LTA-1820SP from Kobelco Research Institute, Inc.) in addition to the electrical resistivity measurement unit 30, was used to perform the microwave photoconductive decay method under the same condition as that in the second embodiment, so that a variation in reflectivity was measured. Subsequently, the specific resistance was measured under the same condition as that in the second embodiment using the configuration of the electrical resistivity measurement unit 30 in FIG. 13, i.e., the electrical resistivity meter (Hiresta from Mitsubishi Chemical Analytech Co., Ltd.) including the electrical resistivity measurement head 31 provided with the up-and-down unit 32 for vertically moving the measurement head. For measuring the specific resistance, the electrical resistivity measurement head 31 was lowered by the up-and-down unit 32 so as to be brought into contact with the oxide semiconductor thin film 20b to measure the specific resistance, and then the electrical resistivity measurement head 31 was raised by the up-and-down unit 32 so as to be separated from the oxide semiconductor thin film 20b for sample change. As a result, the correlation was found as with the second embodiment. In particular, the correlation was able to be more accurately evaluated in the case of using the system of the third embodiment than in the case of separately measuring the specific resistance as in the second embodiment. Although the B value is shown to converge to one point at the best point (in such a case, the absolute value of the B value is maximized) as illustrated in FIG. 11, a higher or lower resistance than the resistance at that point cannot be determined only by the B value in some case. In such a case, a variation in reflectivity is measured by the microwave decay method at the same point on the sample, and resistance is measured using the electrical resistivity meter, and results of the measurements by the two methods are compared to each other, thereby the absolute value can be more accurately evaluated.

LIST OF REFERENCE SIGNS 1 excitation light irradiation unit
3 microwave irradiation unit
4 directional coupler
4a phase regulator
5 magic T
6 first waveguide
6b second waveguide
6c small opening
6d, 6e opening
7 reflected microwave intensity detection unit
8 signal processor
9 evaluation unit
10 stage controller
11 X-Y stage
12 optical path change unit
16a output adjustment power monitor
16b output adjustment unit
20 sample
20a substrate
20b oxide semiconductor thin film
21 excitation light irradiation region
30 electrical resistivity measurement unit
31 electrical resistivity measurement head
32 up-and-down unit 33 measured-value transmission line
41 glass substrate
42 gate insulating film
43 oxide semiconductor layer
44 passivation film (etch stop layer)
45 gate electrode
46 source electrode
47 drain electrode
48 final passivation film
49 contact hole
50 size of oxide semiconductor layer
51 evaluation element
52 glass substrate (mother glass)
53 display
54 excitation light irradiation
55 stop of excitation light irradiation
56 decay waveform
57 peak value

The invention claimed is:

1. A method for evaluating an oxide semiconductor thin film, the method comprising:
a first step of
irradiating excitation light and microwave to an oxide semiconductor thin film,
measuring a maximum of a reflected microwave from the oxide semiconductor thin film, which varies with the irradiation of the excitation light, and
then stopping the irradiation of the excitation light and measuring a temporal variation in the reflectance from the oxide semiconductor thin film after stopping the excitation light irradiation; and
a second step of
calculating a parameter corresponding to slow decay observed after stopping the irradiation of the excitation light based on the temporal variation in the reflectivity, and
evaluating electrical resistivity of the oxide semiconductor thin film.

2. The evaluation method according to claim 1, wherein, in the second step, the parameter corresponding to the slow decay observed at 0.1 to 10 µs after stopping irradiation of the excitation light is calculated based on the variation in reflectivity to evaluate the electrical resistivity of the oxide semiconductor thin film.

3. The evaluation method according to claim 1, wherein the oxide semiconductor thin film contains at least one element selected from the group consisting of In, Ga, Zn, and Sn.

4. The evaluation method according to claim 1, wherein the oxide semiconductor thin film is provided on a surface of a gate insulating film.

5. The evaluation method according to claim 1, wherein a passivation film is provided on a surface of the oxide semiconductor thin film.

6. A method for controlling quality of an oxide semiconductor thin film, wherein the evaluation method according to claim 1 is applied to one of steps of a semiconductor manufacturing process.

7. The evaluation method according to claim 1, wherein the electrical resistivity is one of sheet resistance and specific resistance.

8. The evaluation method according to claim 7, wherein, in the second step, the parameter corresponding to the slow decay observed at 0.1 to 10 µs after stopping irradiation of the excitation light is calculated based on the variation in reflectivity to evaluate the electrical resistivity of the oxide semiconductor thin film.

9. The evaluation method according to claim 7, wherein the oxide semiconductor thin film contains at least one element selected from the group consisting of In, Ga, Zn, and Sn.

10. A method for controlling quality of an oxide semiconductor thin film, wherein the evaluation method according to claim 7 is applied to one of steps of a semiconductor manufacturing process.

11. A system used in the method for evaluating the oxide semiconductor thin film according to claim 7, the system comprising:
an excitation light irradiation unit that irradiates excitation light to a measurement site of an oxide semiconductor thin film with to generate electron-hole pairs in the oxide semiconductor thin film;
a microwave irradiation unit that irradiates a microwave to the measurement site with;
a reflected microwave intensity detection unit that detects intensity of a reflected microwave from the oxide semiconductor thin film due to reflection of the microwave, the intensity being varied by the excitation light irradiation; and
an unit for evaluating electrical resistivity of the oxide semiconductor thin film based on detection data of the reflected microwave intensity detection unit.

12. An evaluation element being used in the evaluation method according to claim 1, and including an oxide semiconductor thin film provided on a substrate.

13. The evaluation element according to claim 12, wherein the oxide semiconductor thin film is directly provided on a surface of a gate insulating film.

14. The evaluation element according to claim 12, wherein a passivation film is provided on a surface of the oxide semiconductor thin film.

15. An evaluation device, comprising a plurality of evaluation elements arranged on a substrate, each of the evaluation elements being the evaluation element according to claim 12.

16. The evaluation element according to claim 12, wherein the oxide semiconductor thin film is directly provided on a surface of the substrate.

17. The evaluation element according to claim 16, wherein a passivation film is provided on a surface of the oxide semiconductor thin film.

18. An evaluation device, comprising a plurality of evaluation elements arranged on a substrate, each of the evaluation elements being the evaluation element according to claim 16.

19. A system used in the method for evaluating the oxide semiconductor thin film according to claim 1, the system comprising:
an excitation light irradiation unit that irradiates excitation light to a measurement site of an oxide semiconductor thin film with to generate electron-hole pairs in the oxide semiconductor thin film;
a microwave irradiation unit that irradiates a microwave to the measurement site with;
a reflected microwave intensity detection unit that detects intensity of a reflected microwave from the oxide semiconductor thin film due to reflection of the microwave, the intensity being varied by the excitation light irradiation; and
an unit for evaluating electrical resistivity of the oxide semiconductor thin film based on detection data of the reflected microwave intensity detection unit.

20. The system for evaluating the oxide semiconductor thin film according to claim 19, further comprising an electrical resistance measurement unit having an electrical resistivity measurement head and an up-and-down unit for the electrical resistivity measurement head.

* * * * *